United States Patent [19]

Castrogiovanni et al.

[11] Patent Number: 5,225,186

[45] Date of Patent: Jul. 6, 1993

[54] HIGH COSMETIC POWDER LIPSTICK COMPOSITION

[75] Inventors: Anthony Castrogiovanni, Belford; Craig D. Arpino, North Brunswick; Joseph F. Calello, Union, all of N.J.

[73] Assignee: Revlon Consumer Products Corporation, New York, N.Y.

[21] Appl. No.: 705,217

[22] Filed: May 24, 1991

Related U.S. Application Data

[63] Continuation of Ser. No. 541,612, Jun. 21, 1990, abandoned.

[51] Int. Cl.⁵ .............................................. A61K 7/025
[52] U.S. Cl. ........................................ 424/64; 424/63; 424/DIG. 5
[58] Field of Search ................. 424/64, 70, 63, 59, 424/DIG. 5, 69, 401

[56] References Cited

U.S. PATENT DOCUMENTS

| | | | |
|---|---|---|---|
| 4,137,302 | 1/1977 | Humbert et al. | 424/70 |
| 4,431,673 | 2/1984 | Goldner et al. | 424/63 |
| 4,578,266 | 3/1986 | Tietjen et al. | 424/DIG. 5 |
| 4,699,780 | 10/1987 | Jennings et al. | 424/63 |
| 4,837,011 | 6/1989 | Macchio et al. | 424/69 |
| 4,892,726 | 1/1990 | Yonekuna et al. | 424/63 |
| 4,919,934 | 4/1990 | Deckner et al. | 424/401 |
| 4,944,937 | 7/1990 | McCall | 424/59 |
| 5,023,075 | 6/1991 | Macchio et al. | 424/69 |
| 5,034,216 | 7/1991 | Barone et al. | 424/63 |
| 5,039,518 | 8/1991 | Barone et al. | 424/63 |

Primary Examiner—Thurman K. Page
Assistant Examiner—D. Colucci
Attorney, Agent, or Firm—Julie Blackburn

[57] ABSTRACT

A stick shaped lipstick composition which comprises a higher loading of cosmetic powders than those available in prior art compositions is disclosed. The composition includes between about 10% and about 65% of at least one cosmetic powder. At least one low viscosity liquid carboxylic acid ester, present in a concentration of between about 10% and about 65%, is also included. A third component of the composition is at least one high viscosity surface oil included in an amount of between about 1% and about 18%. The composition additionally comprises between about 2% and about 15% of at least one plasticizing agent. All of the above mentioned percentages are by weight, based on the total weight of the composition. The high concentration of cosmetic powder provides a unique finish, texture and feel lipstick heretofore unavailable in convenient stick shape.

11 Claims, No Drawings

5,225,186

HIGH COSMETIC POWDER LIPSTICK COMPOSITION

This is a continuation of copending application(s), Ser. No. 07/541,612 filed on Jun. 21, 1990, now abandoned.

BACKGROUND OF THE INVENTION

1. Field of the Invention

This invention relates to stick shaped lipstick cosmetic products which are designed to provide relatively high concentrations of powdered components and which provide both the unique finish (visual appearance), texture and feel of a pressed powder cosmetic product.

Stick shaped lip cosmetic products have been molded or produced in a variety of shapes and sizes ranging from slimline versions to the standard size bullet configuration. A common limitation of the prior art lipstick formulations, however, has been the relatively low amount of cosmetic powder materials that can be readily incorporated into such products. Incorporating powders at levels of about 20% to 30% by weight or more into prior art stick products has generally resulted in poor moldability, poor structure and poor product comfort or performance for the user.

At the present time, commercially available lip powders have been limited to those that are marketed in other than a stick shaped configuration. Lip powder products on the market today are typically presented in a pressed powder compact form to be applied with an applicator. This compact form of lip product is limiting and is not as generally accepted for use as is the stick form of lip product, i.e., lipstick. Therefore, there is a need for a stick product that will apply cosmetic powders to the lips and thereby provide finishes that were heretofore theoretically obtainable only in pressed powder compact form.

An object, therefore, of the present invention is to provide a stick shaped lipstick product which has a relatively high content of cosmetic powder.

A further object of the present invention is to provide a stick shaped lipstick product which will provide finishes to the lips that have, heretofore, only been available from pressed powder products.

2. Description of the Prior Art

Japanese Patent Application 61257908 to Shiseido KK, published Nov. 15, 1986 discloses a make-up cosmetic composition, which may be a lipstick, which employs therein certain two-component powdery materials formed from an organic particulate or an inorganic nucleus material having a particle size of 1-100 microns, which nucleus material is coated with a particulate organic or inorganic powder material, such second particulate material having a particle size 1/5 that of such first particulate material.

U.S. Pat. Nos. 4,659,562 and 4,820,510 disclose cosmetic make-up compositions containing finely divided silica and finely divided polyethylene fibers.

Japanese Patent Application 56081512 to Sakata KK, published Jul. 3, 1981 discloses a cosmetic material which contains porous globular granules, the surface of which has been rendered lyophobic.

SUMMARY OF THE INVENTION

The present invention relates to a stick shaped lipstick product which comprises a high concentration of cosmetic powder components and a selected combination of other components designed to enable the final formulation to be molded into a stick shaped configuration that provides powder-type finishes to the lips.

In accordance with the present invention a stick shaped lipstick composition is provided. The lipstick composition comprises between about 15% and about 80% of at least one cosmetic powder; between about 10% and about 65% of at least one low viscosity liquid carboxylic acid ester; between about 1% and about 18% of at least one high viscosity surface oil; and between about 2% and about 15% of at least one plasticizing agent, all said percentages being by weight, based on the total weight of the lipstick composition.

DETAILED DESCRIPTION

The stick shaped lipstick composition of the present invention includes between about 15% and about 80%, which, it should be appreciated, denotes percentage by weight, based on the total weight of the composition, of at least one cosmetic powder. Preferably, the cosmetic powder constituent of the composition represents between about 25% and about 45% by weight of the composition.

Cosmetic powders within the contemplation of the present invention include mica, talc, bismuth oxychloride, bentonite, nylon, silica, acrylates copolymer and mixtures thereof. It should be understood that the above recited cosmetic powders encompass all materials within the meaning of those names as set forth in the CTFA Cosmetic Ingredient Dictionary, Third Edition, published by the Cosmetic, Toiletry and Fragrance Association, Inc., Washington, D.C. (1982), which is incorporated herein by reference. For example, mica, as defined in the CTFA Cosmetic Ingredient Dictionary, 3rd Ed., includes uncoated mica as well as titanated mica, that is, mica coated with titanium dioxide.

It is emphasized that the CTFA Cosmetic Ingredient Dictionary, Third Edition in defining mica as including titanated mica, that is, mica coated with titanium dioxide, emphasizes that not only may the cosmetic powder constituent be comprised of mica in whole or in part but, also, that the cosmetic powder component of the lipstick composition may be wholly or partially titanated mica. Those skilled in the art are aware that titanated mica provides a "frost" appearance that many users find attractive.

A recently approved CTFA ingredient not included in the aforementioned CTFA Cosmetic Ingredient Dictionary, Third Edition, that is within the contemplation of the cosmetic powder component, useful in the present lipstick composition, is teflon. It is anticipated that this ingredient will be included in the next published edition of the Dictionary.

In a preferred embodiment, some or all of the cosmetic powder included in the lipstick composition may be coated with a hydrophobic agent. The hydrophobic agent coating of some or all of the cosmetic powder component not only imparts hydrophobicity, a desirable attribute for a lipstick, but, in addition, provides the lipstick composition with smoother texture and improves the lipstick composition's moisturization characteristic.

In the preferred embodiment wherein the cosmetic powder is coated with a hydrophobic agent, the degree of coating is such that the hydrophobic agent comprises between about 1% and about 5% by weight, based on the total weight of the hydrophobic coated cosmetic powder. More preferably, the concentration of the hydrophobic agent is in the range of between about 1.5% and about 3% by weight.

Among the hydrophobic agents preferred for use in coating the cosmetic powders within the contemplation of the stick lipstick composition are 6-aminocaproic acid, lecithin, a mixture of cyclomethicone and mineral oil, preferably a 1:99 weight mixture of mineral oil to cyclomethicone. Again, these hydrophobic agents are set forth in the CTFA Cosmetic Ingredient Dictionary, 3rd Ed., incorporated herein by reference.

The cosmetic powder component of the stick lipstick composition, independent of its identity, whether it is coated or not, is preferably characterized by a particle size of less than about 30 microns. More preferably, the particle size of the cosmetic powder component is in the range of between about 1 micron and about 25 microns.

Another essential component of the stick shaped lipstick composition is at least one liquid, low viscosity carboxylic acid ester. The ester component, present in the composition in a concentration of between about 10% and about 65% by weight, based on the total weight of the lipstick composition, is preferably characterized by a viscosity, at 25° C., in the range of between about 5 centipoise (cp) and about 100 cp. More preferably, the liquid low viscosity carboxylic acid ester is present in a concentration of between about 25% and about 45% by weight.

The carboxylic acid ester component serves to wet out the cosmetic powder component and significantly contribute to the light, dry, silky and powdery texture of the final lipstick product. In addition, the liquid ester component performs in such a way to promote better adhesion and wear of the lipstick composition to the lips of the user. The ester component further contributes to the moisturizing effect of the lipstick composition on the lips to which it is applied.

Among the liquid, low viscosity carboxylic acid esters that can be used in the lipstick composition are isotridecyl isononanoate, isostearyl neopentanoate, cetyl octanoate, glyceryl trioctanoate, isodecyl oleate and isodecyl neopentanoate, ingredients mentioned in the CTFA Ingredient Dictionary, 3rd Edition incorporated herein by mentioned reference. In addition, mixtures of these esters, as well as PEG-4 diheptanoate, tridecyl neopentanoate, isohexyl neopentanoate and tridecyl octanoate, ingredients which are not included in the Third Edition but will appear in the next edition of the CTFA Ingredient Dictionary, can be used with each other or with one or more of the esters, recited above, already included in the 3rd Edition, to provide the ester component of the lipstick composition.

A third critical ingredient of the lipstick composition is at least one high viscosity surface oil. The surface oil component comprises one or more surface oils which are characterized by a viscosity, at 25° C., in the range of between about 200 cp. and about 250,000 cp. The surface oil component contributes emolliency to the lipstick composition. To that end, the surface oil component comprises between about 1% and about 18% by weight of the total weight of the lipstick composition. More preferably, the surface oil component comprises between about 3% and about 10% by weight of the total composition.

The surface oils employable as the surface oil component of the lipstick composition of the present invention include castor oil, lanolin, sorbitan sesquioleate and mixtures thereof. These ingredients are fully defined in the aforementioned CTFA Cosmetic Ingredient Dictionary, 3rd Ed., incorporated herein by reference. In addition to these surface oils, another such oil, triisocetyl citrate, which will appear in the next edition of the Dictionary, may be utilized alone or with one or more of the surface oils mentioned above.

A fourth and last essential component of the lipstick of the present invention is a plasticizing agent. The plasticizing agent aids in providing smoothness to the lipstick composition, plasticizing as it does the hard components contained therein.

To provide this effect, at least one plasticizing agent is included in the lipstick composition in a concentration in the range of between about 2% and about 15% by weight based on the total weight of the lipstick composition. More preferably, the plasticizing component represents between about 5% and about 12% by weight of the lipstick composition.

Among the plasticizers contemplated for use in the lipstick composition are a mixture of acetylated lanolin alcohol and cetyl acetate, caprylic/capric triglyceride, oleyl alcohol, lanolin alcohol, octyldodecanol and mixtures thereof. Definitions of these preferred plasticizers are provided by the CTFA Cosmetic Ingredient Dictionary, Third Ed., incorporated herein by reference.

Of these plasticizers, a mixture of acetylated lanolin alcohol and cetyl acetate is particularly preferred for use in the lipstick composition. Still more preferably, an admixture of between about 10% and about 30% by weight, based on the total weight of the admixture, of acetylated lanolin alcohol and between about 70% and about 90% by weight, again based on the total weight of the admixture, cetyl acetate is utilized as the plasticizer component.

In a preferred embodiment the lipstick composition includes spherical silica. It should be appreciated that spherical silica, which has not yet been included in the CTFA Cosmetic Ingredient Dictionary but has been approved for use in cosmetic applications and thus will appear in the next edition of the Dictionary, has an average particle size of between about 1 micron and about 20 microns. More preferably, in the preferred embodiment wherein spherical silica is included in the lipstick composition, it is present in an average particle size range of between about 3 microns and about 15 microns.

The inclusion of spherically shaped silica is preferred in that it significantly increases the ease of application of the lipstick. Those skilled in the art are aware of a major detriment to the use of high cosmetic powder-containing lipsticks in the prior art has been the difficulty of application. Lipstick compositions in the prior art which comprised high concentrations of cosmetic powders tended to be dry and scratchy, causing irritation upon application. The inclusion of spherical silica provides a "rollerball" effect minimizing friction, thus promoting ease of application of a powdered product to the lips. Spherical silica also is believed to selectively absorb oils both in the product and on the lips which helps facilitate controlled application and quality of wear (i.e. minimal bleeding and feathering).

In the preferred embodiment wherein spherical shaped silica is incorporated in the lipstick composition it is preferably present in a concentration in the range of between about 0.5% and about 20% by weight, based on the total weight of the lipstick composition. More preferably, the spherical shaped silica constituent is present in the range of between about 1% and about 10% by weight of the composition.

Another preferred ingredient of the lipstick composition is wax. Wax is provided to provide structural stability by binding, solidifying and hardening the other components of the composition. In the preferred embodiment wherein a wax component is incorporated into the lipstick composition it is present in a concentration of between about 5% and about 20% by weight, based on the total weight of the lipstick composition. More preferably, the wax constituent comprises between about 9% and about 15% by weight.

Among the waxes that can be employed as the wax constituent of the lipstick composition are carnauba, ceresin, PEG-20 sorbitan beeswax, paraffin, microcrystalline wax, glyceryl tribehenate, candelilla wax and mixtures thereof. Each of these components are included and defined in the CTFA Cosmetic Ingredient Dictionary, Third Edition, incorporated by reference.

Another preferred ingredient of the lipstick composition is a pigment component. One or more pigments, providing between about 0.5% and about 10% by weight of the total composition, is preferably included to provide the desired color shade to the lipstick composition. More preferably, the pigment constituent represents between about 1% and about 7% by weight of the lipstick composition.

Among the preferred ingredients within the contemplation of the pigment component are iron oxides, D&C Red No. 7 calcium lake, D&C Red No. 6 barium lake, D&C Red No. 27 aluminum lake, D&C Red No. 33 aluminum lake, D&C Red No. 30 lake, FD&C Yellow No. 6 aluminum lake, FD&C Blue No. 1 aluminum lake, D&C Orange No. 5, D&C Red No. 21 and D&C Red No. 27. One or a mixture of two or more of these pigments is preferably utilized in the lipstick composition.

It should be appreciated that each of these pigments is defined in the CTFA Cosmetic Ingredient Dictionary, Third Edition incorporated herein by reference. Furthermore, it should also be understood that iron oxides and selected organic colorants of choice may be included in the composition as a coating on one or more of the cosmetic powder ingredients that constitute the cosmetic powder component of the lipstick composition. Indeed, in a preferred embodiment, iron oxides colorant is coated onto mica and/or bismuth oxychloride.

Yet another preferred component of the stick shaped lipstick composition is at least one antioxidant. Preferred antioxidants include BHA and ascorbyl palmitate, defined in the CTFA Cosmetic Ingredient Dictionary, Third Edition, and Vitamin E acetate, a cosmetically acceptable ingredient which will be included in the next edition of the CTFA Cosmetic Ingredient Dictionary.

The antioxidant component, which is included to bar deterioration of the lipstick composition by oxidation, when present in the stick lipstick composition, represents between about 0.05% and about 0.5% by weight of the total weight of the composition. More preferably, the antioxidant component constitutes between about 0.1% and about 0.2% by weight of the composition.

Still another preferred component of the lipstick composition is the preservative component. The preservative component, provided by one or more of the below mentioned ingredients, defined in the CTFA Cosmetic Ingredient Dictionary, Third Edition, insures that the lipstick composition will be free of microorganism infestation. Ingredients that provide this preservative function include methylparaben, ethylparaben, propylparaben, butylparaben and mixtures thereof.

The preservative component, when present, is included in a weight concentration in the range of between about 0.05% and about 1%, more preferably, between about 0.1% and about 0.6%, said percentages being by weight, based on the total weight of the lipstick composition.

A final preferred ingredient is one or more fragrances. The fragrance component provides the lipstick composition with the desired taste and aroma commonly provided by lipstick compositions. The fragrance component, because of the wide range of possible ingredients having stronger or weaker aromas, may vary in a concentration range, when present, of from about 0.01% to about 2% by weight. More preferably, 0.1% to about 1.25% by weight, based on the total weight of the composition, is fragrance.

The stick shaped lipstick composition is preferably formulated by combining various components in subcompositions which are then combined to produce the composition of the present invention.

The first such subcomposition is prepared by homogeneously melt blending together, at a temperature in the range of between about 80° C. and about 90° C., the wax component, the low viscosity ester component, the plasticizing agent component, preservatives and antioxidants and a fraction of the high viscosity surface oil component.

The second subcomposition, if present, comprises the fraction of the high viscosity surface oil component not added in the first subcomposition.

The third subcomposition comprises a fraction of the cosmetic powder component and, if present, the colorant agent component, which are combined in a homogenous mixture.

The fourth subcomposition includes the remainder of the cosmetic powder component and, if preferably present, the spherical silica component. The fourth subcomposition is combined into a homogeneous solid admixture.

Finally, the fifth subcomposition is present if the lipstick composition includes a fragrance component. The fifth subcomposition constitutes the fragrance component.

In the formation of the lipstick composition the second and third subcompositions are homogeneously admixed, preferably by means of a roller mill, and added, under agitation, to the first subcomposition. The resultant composition is melt blended to form a molten homogeneous mixture. This molten mixture is blended with the fourth subcomposition to produce a fragrance-free intimately mixed composition. If a fragrance is included, it, constituting the fifth subcomposition, is blended with the molten admixture of the first four subcompositions to produce the final lipstick composition.

A preferred stick shaped lipstick composition, made in accordance with the above procedure, employing preferred ingredients discussed above, includes between about 31% and about 35% cosmetic powders, which include mica, lecithin, bismuth oxychloride coated mica and bentonite; between about 19% and about 23% low viscosity liquid carboxylic acid esters including isotridecyl isononanoate and PEG-4 diheptanoate; between about 15% and about 19% high viscosity surface oil including lanolin, castor oil, sorbitan sesquioleate and triisocetyl citrate; between about 9% and about 13% plasticizing agents including a mixture of acetylated lanolin alcohol and cetyl citrate; between about 1% and about 3% spherical silica; between about 10% and about 14% waxes including carnauba, ceresin and PEG-20 sorbitan beeswax; between about 1% and about 10% pigment including D&C Red No. 6 barium lake and D&C Red No. 7 calcium lake; between about 0.05% and about 0.15% antioxidant including BHA; between about 0.2% and about 0.6% preservative including methylparaben and propylparaben; and between about 0.1% and about 0.5% fragrance. It is emphasized that all the percentages recited above are by weight, based on the total weight of the composition.

The following example is given to illustrate the present invention. Because this example is provided for illustrative purposes only, the scope of the present invention should not be limited thereto.

EXAMPLE

Preparation of a Stick Shaped Lipstick Composition

A lipstick composition was prepared by melt blending together in a suitable container, provided with agitation and heating means, the following constituents in the recited number of parts by weight to produce a first subcomposition.

| Ingredient | Parts by Wt. |
| --- | --- |
| Carnauba | 1.5 |
| Ceresin | 10.0 |
| PEG-20 sorbitan beeswax | 1.0 |
| Acetylated lanolin alcohol | 2.0 |
| Cetyl acetate | 9.0 |
| Isotridecyl isononanoate | 7.5 |
| PEG-4 diheptanoate | 13.0 |
| Triisocetyl citrate | 6.0 |
| Lanolin | 1.0 |
| Castor oil | 2.7 |
| Methylparaben | 0.3 |
| Propylparaben | 0.1 |
| BHA | 0.1 |

A second subcomposition was prepared by blending together, in a separate container, 1.0 part by weight sorbitan sesquioleate and 7.5 parts by weight castor oil. This subcomposition was, in turn, blended with a third subcomposition formed by mixing together the pigment coloring agents, 1.2 parts by weight D&C Red No. 6 barium lake and 0.6 part by weight D&C Red No. 7 calcium lake, with 0.25 part by weight bentonite. The resultant blend of the second and third subcompositions was introduced into the vessel containing the molten mixture of the first subcomposition.

A fourth subcomposition comprising 1.75 parts by weight spherical silica; 31.0 parts by weight mica and 2.2 parts by lecithin treated mica was prepared by dry blending. This solid blend, the fourth subcomposition, was added to the contents of the vessel containing the molten mixture of the first three subcompositions and mixed until a homogeneous mixture of the four subcompositions was obtained.

Finally, 0.3 part by weight of a fragrance was added to the result subcomposition to produce the final composition.

The final composition was molded into a stick lipstick.

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. An anhydrous stick shaped lip cosmetic composition consisting essentially of between about 15% and about 80% of at least one cosmetic powder selected from the group consisting of mica, talc, bismuth oxychloride, bentonite, nylon, silica, acrylates copolymer, teflon, spherical silica, and mixtures thereof;

between about 10% and about 65% of at least one low viscosity liquid carboxylic acid ester having a viscosity of 5 to 100 cp at 25° C. and selected from the group consisting of isotridecyl isononanoate, isostearyl neopentanoate, cetyl octanoate, glyceryl trioctanoate, isodecyl oleate, isodecyl neopentanoate, PEG-4 diheptanoate, tridecyl neopentanoate, isohexyl neopentanoate, tridecyl octanoate, and mixtures thereof;

between about 1% and about 18% of at least one high viscosity surface oil having a viscosity of 200 to 250,000 cp at 25° C. selected from the group consisting of castor oil, lanolin, sorbitan sesquioleate, triisocetyl citrate, and mixtures thereof; and between about 2% and about 15% of at least one plasticizing agent selected from the group consisting of acetylated lanolin alcohol, cetyl acetate, caprylic/capric triglyceride, oleyl alcohol, lanolin alcohol, octyldodecanol, or mixtures thereof;

between about 5% and about 20% of a wax selected from the group consisting of carnauba, ceresin, PEG-20 sorbitan beeswax, paraffin, microcrystalline wax, glyceryl tribehenate, candelilla wax, and mixtures thereof; a pigment, antioxidant, preservative, and fragrance.

2. A composition in accordance with claim 1 wherein said cosmetic powder is coated with a hydrophobic agent selected from the group consisting of 6-aminocaproic acid, lecithin, cyclomethicone, mineral oil, or mixtures thereof.

3. A composition in accordance with claim 1 wherein the spherical silica is of particle size 1-20 microns and is present in an amount of 0.5-20%.

4. An anhydrous stick shaped lip cosmetic composition consisting essentially of between about 25% and about 45% of a cosmetic powder selected from the group consisting of mica, talc, bismuth oxychloride, bentonite, nylon, silica, acrylates copolymer, teflon and mixtures thereof;

between about 25% and about 45% of a liquid carboxylic acid ester selected from the group consisting of isotridecyl isononanoate, isostearyl neopentanoate, cetyl octanoate, glyceryl trioctanoate, isodecyl oleate, isodecyl neopentanoate, PEG-4 diheptanoate, tridecyl neopentanoate, isohexyl neopentanoate, tridecyl octanoate and mixtures thereof;

between about 3% and about 10% of a surface oil selected from the group consisting of castor oil, lanolin, sorbitan sesquioleate, triisocetyl citrate, and mixtures thereof; and between about 5% and about 12% of a plasticizing agent selected from the group consisting of a mixture of acetylated lanolin alcohol and cetyl acetate, caprylic/capric triglyceride, oleyl alcohol, lanolin alcohol, octyldodecanol and mixtures thereof, between about 5% and about 20% wax selected from the group consisting of carnauba, ceresin, PEG-20 sorbitan beeswax, paraffin, microcrystalline wax, glyceryl tribehenate, candelilla wax, and mixtures thereof and a pigment, fragrance, antioxidant, and preservative;

all said percentages being by weight, based on the total weight of said composition.

5. A composition in accordance with claim 4 comprising between about 0.5% and about 20% of spherical silica having an average particle size in the range of between about 1 micron and about 20 microns.

6. A composition in accordance with claim 5 wherein said spherical silica is present in a concentration of between about 1% and about 10% and has an average particle size of between about 3 microns and about 15 microns.

7. A composition in accordance with claim 4 comprising between about 1% and about 7% of pigments selected from the group consisting of iron oxides, D&C Red No. 7 calcium lake, D&C Red No. 6 barium lake, D&C Red No. 27 aluminum lake, D&C Red No. 33 aluminum lake, D&C Red No. 30 lake, FD&C Yellow No. 6 aluminum lake, FD&C Blue No. 1 aluminum lake, D&C Orange No. 5, D&C Red No. 21, D&C Red No. 27 and mixtures thereof.

8. A composition in accordance with claim 7 comprising between about 0.1% and about 0.2% of an antioxidant selected from the group consisting of butylated hydroxy anisole, ascorbyl palmitate and Vitamin E acetate.

9. A composition in accordance with claim 8 comprising between about 0.1% and about 0.6% of a preservative selected from the group consisting of methylparaben, ethylparaben, propylparaben, butylparaben and mixtures thereof.

10. A composition in accordance with claim 9 comprising between about 0.1% and about 1.25% of a fragrance.

11. A composition in accordance with claim 4 wherein said cosmetic powder is coated with a hydrophobic agent selected from the group consisting of 6 aminocaproic acid, lecithin, and a mixture of cyclomethicone and mineral oil, said hydrophobic agent coating representing between about 1% and about 5% by weight of said hydrophobic coated cosmetic powder.

* * * * *